United States Patent [19]

Milam et al.

[11] 4,017,551

[45] Apr. 12, 1977

[54] LIQUID PHASE CHLORINATION OF AROMATIC HYDROCARBONS USING MANGANESE CHLORIDE CATALYST

[75] Inventors: Joseph E. Milam, New Martinsville, W. Va.; Gordon A. Carlson, Wadsworth, Ohio

[73] Assignee: PPG Industries, Inc., Pittsburgh, Pa.

[22] Filed: Jan. 27, 1975

[21] Appl. No.: 544,244

[52] U.S. Cl. .......................... 260/650 R; 252/441; 260/649 R
[51] Int. Cl.² ........................................ C07C 25/08
[58] Field of Search ............................... 260/650 R

[56] References Cited

UNITED STATES PATENTS

| | | | |
|---|---|---|---|
| 1,963,761 | 6/1934 | Prahl | 260/650 R |
| 2,046,411 | 7/1936 | Ramage | 260/650 R |
| 3,214,482 | 10/1965 | Caropreso et al. | 260/650 R |

*Primary Examiner*—D. Horwitz
*Attorney, Agent, or Firm*—Roger S. Benjamin

[57] ABSTRACT

A process for the liquid phase nuclear chlorination of benzenes which uses a novel manganese chloride catalyst in an iron-free reaction environment. The manganese chloride catalyst provides a dichlorobenzene product having a higher ratio of orthodichlorobenzene to paradichlorobenzene than is obtained with conventional commercial liquid phase chlorination catalysts.

14 Claims, No Drawings

LIQUID PHASE CHLORINATION OF AROMATIC HYDROCARBONS USING MANGANESE CHLORIDE CATALYST

BACKGROUND OF THE INVENTION

This invention relates generally to nuclear chlorine substitution reactions of aromatic hydrocarbons and in particular to the formation of dichlorobenzenes from benzene or monochlorobenzene feedstocks.

Orthodichlorobenzene is useful as a solvent, heat exchange media and chemical intermediate for synthesis of herbicides. Commercial liquid phase nuclear chlorination processes producing dichlorobenzenes yield a product distribution wherein para-isomer considerably predominates over the ortho-isomer. It is desirable to adjust the ratio of dichlorobenzene isomers to promote formation of the ortho-isomer in the product.

The nuclear chlorine substitution of benzenes to form dichlorobenzenes is conventionally performed in a liquid phase process by contacting gaseous chlorine with benzene or monochlorobenzene in the presence of a ferric chloride or aluminum chloride catalyst, for example, as described by Wiegandt, H. F. and Lantos, P. R., et al., *Industrial J Engineering Chem.*, Vol. 43, p. 2167-72, 1951. The ferric chloride liquid phase catalyzed dichlorobenzene formation typically has a ratio of para- to ortho- isomers of about 1.4 and above.

Substitution type chlorination reactions of benzene also produce some monochlorobenzene, metadichlorbenzene and poly-chlorinated (three or more chlorine atoms) benzenes. Monochlorobenzene may be recycled to the reaction zone. It is desirable to minimize the formation of the metaisomer because it interferes with the separation by distillation of the para-isomer. The polychlorobenzenes have marginal industrial value.

Manganese has been employed in chlorination processes. For example, manganese oxide has a described utility for producing a high yield of paradichlorobenzene (U.S. Pat. No. 2,046,411 issued to W. D. Ramage). In addition, manganese chloride is described as a chlorination promoter in the presence of ferric chloride (U.S. Pat. No. 3,214,482 issued to F. E. Caropreso).

SUMMARY OF THE INVENTION

An embodiment of this invention is a liquid phase nuclear chlorination process for aromatic hydrocarbons. An especially desirable process is the chlorination of benzene or monochlorobenzene to dichlorobenzenes. The dichlorobenzene product produced by the process of this invention has a higher proportion of orthodichlorobenzene to paradichlorobenzene (equivalent to a lower "p/o" ratio) than is achieved by conventional liquid phase chlorination processes. In addition, the process yields less metadichlorobenzene in proportion to paradichlorobenzene and less polychlorobenzenes in proportion to the total dichlorobenzenes produced.

An embodiment of this invention is a liquid phase manganese chloride chlorination catalyst productive of low p/o ratios.

A further embodiment of this invention is a particular method of preparing the manganese chloride catalyst composition used for the chlorination of aromatic hydrocarbons, particularly benzene and monochlorobenzene.

An additional embodiment of this invention is a feedstock mixture suitable for the formation of dichlorobenzene having a low p/o ratio.

Reactants

Suitable reactants are aromatic hydrocarbons capable of nuclear chlorine substitution. Included within the term "aromatic hydrocarbons" are chlorinated aromatic hydrocarbons capable of further nuclear chlorine substitution. Illustrative aromatic hydrocarbons are benzene, monochlorobenzene, naphthalene, phenanthrene, xylene, anthracene, toluene or biphenyl. Benzene and monochlorobenzene are preferred feedstocks and may be supplied to the reactor separately or mixed in any proportion. The monochlorobenzene used as feedstock may be prepared by any prior art method.

Chlorine is conveniently supplied to the reaction as a gas. The p/o ratio remains essentially the same whether a deficiency or surplus of chlorine is supplied. In practice, a stoichiometric quantity of chlorine is preferred. The reaction rate may be controlled by the rate at which chlorine is introduced to the reactor. However, chlorine introduced at an excessive rate will carry-over from the reaction zone and contaminate the by-product HCl.

The Reactor and Related Equipment

The liquid phase chlorination reactor may assume a conventional configuration (see; *Industrial and Engineering Chem.*, supra). Reactor design should allow for the introduction of chlorine, catalyst, and aromatic hydrocarbon and the removal of by-product HCl and chlorinated product. Provision for cooling and agitating the reaction mass is desirable. The reactor may be adapted to batch, semi-batch or continuous operation.

All materials of construction should be iron-free. By the term, "iron-free" is meant construction material which will not under the described reaction conditions admit a catalytically active quantity of iron into the reaction zone. It has been determined that the iron concentration in the reaction media should not be above about 3 per million when the catalyst of this invention is used. Illustrative materials suitable for reactor fabrication are glass and nickel.

The Catalyst

The catalyst composition of this invention comprises manganese chloride in an iron-free reaction environment. The term "manganese chloride" includes all oxidation states of manganese with chlorine and hydrated compounds are, $MnCl_2$ (anhydrous), $MnCl_2 \cdot H_2O$, $MnCl_2 \cdot 2H_2O$, $MnCl_2 \cdot 3 H_2O$, $MnCl_2 \cdot 3.5 H_2O$, $MnCl_2 \cdot 4 H_2O$ and $MnCl_3$. The manganese chloride compounds may be used in combination in a catalyst composition.

It is preferred to introduce the manganese chloride in substantially anhydrous form. A preferred method of making the substantially anhydrous manganese chloride catalyst composition comprises the steps of dehydrating hydrated (preferably a polyhydrated) $MnCl_2$ by reaction with thionyl chloride and removing the hydrolysis products of the thionyl chloride and residual thionyl chloride from the dehydrated manganese chloride (see; Therard Moeller (Editor), *Inorganic Synthesis*, Vol. V, p. 154, McGraw-Hill, New York 1957). The resulting substantially anhydrous manganese chloride catalyst composition is introducted into the reaction zone.

The manganese chloride catalyst may be recovered and recycled to the reaction zone. The catalyst may be recovered and regenerated by any suitable method, for example, washing the product with water, reacting the wash water with a soluble hydroxide, and subsequently reacting the precipitated hydroxide with HCl. Catalyst concentration is not critical to the production of low p/o ratios, however, it is generally preferred to employ the manganese chloride catalyst composition at a concentration of from about 0.05 to 20 percent by weight (calculated as weight of anhydrous $MnCl_2$ based on the weight of liquid media in the reaction zone). As a matter of practice, catalyst concentrations greater than 20 percent by weight will rarely be used although such high concentrations are operative. If desired, the catalyst may be formed on a suitable support such as alumina, zeolites, activated carbon, etc.

The Halogen Substituted Reaction Products

The dichlorobenzene reaction products prepared utilizing manganese chloride catalyst compositions have p/o ratios below 1.35 to as low as about 0.8 depending upon the selection of reaction conditions. The product mixture is conveniently separated by conventional distillation and crystallization techniques. Chlorinated product having insufficient chlorine substitution may be recycled to the reaction zone together with unreacted benzene or monochlorobenzene feedstock.

Metadichlorobenzene

Metadichlorobenzene constitutes an undesired portion of the reaction product. Manganese chloride catalyst compositions tend to minimize the proportion of meta isomer in relation to para isomer.

Polychlorobenzenes

Benzene and monochlorobenzene are preferably chlorinated to a level somewhat less than two chlorine atoms per benzene nucleus when dichlorobenzene product is desired. Nuclear halogen substitution reactions yield a range of products. Chlorination to high levels tends to form an increasing proportion of trichlorobenzene and higher substitution products. It is preferred practice to chlorinate to a level less than desired in the major product. This chlorination level may be monitored by continuously sampling the reaction products and/or adjusting the amount of chlorine admitted to the reaction vessel.

Moisture

The introduction of water in controlled minor amounts to a reaction zone containing manganese chloride is beneficial to the production of dichlorobenzenes having low p/o ratios.

Water is preferably introduced into the reaction zone as moisture contained in the aromatic feedstock. This procedure has the added convenience that extensive drying of the feedstock is not required. It is preferred to operate the process with an anhydrous manganese chloride catalyst and a feedstock containing about 10 to about 500 parts per million of water. Alternatively, water may be added to the reaction zone as water of hydration in the manganese chloride catalyst. $MnCl_2$ forms a series of hydrates including the 4-, 3.5-, 3-, 2- and 1-hydrates. The mono-hydrate is comparatively stable and resistant to dehydration. If desired, water may be added to the reaction zone as $MnCl_2$ containing between 0.8 and 1.5 moles of water of hydration.

Combination of Reactants

The elemental chlorine, benzene or monochlorobenzene feed, moisture and manganese chloride catalyst composition may be combined in any order either before or within the iron-free reaction zone. If desired, a dichlorobenzene forming mixture having dissolved chlorine and suspended catalyst may be prepared. Upon heating, the mixture will form dichlorobenzenes having a low p/o ratio.

Interfering Substances

A variety of materials show some catalytic effect in promoting chlorination substitution reactions of benzenes. The requirement for an iron-free system has been described, but it is also desirable to conduct the chlorination reaction in the absence of catalytically effective amounts of any liquid phase chlorination substitution catalyst which is productive of p/o ratio above about 1.4 or above. This invention may be advantageously operated using solely manganese chloride in the catalyst composition. Concurrent use of catalysts having chlorination rates below that of manganese chloride is not desirable. In particular, it is preferable to exclude catalytically effective amounts of compounds derived from aluminum, sulfur, gallium, molybdenum, tin, antimony, tellurium, samarium, zinc, copper, phosphorous, and iodine in the reaction medium.

Effect of Temperature

The reaction temperature has a pronounced effect on the p/o ratio of the dichlorobenzene product. The manganese chloride catalyzed reaction system displays sensitivity to temperature with an optimum in the vicinity of 50° C. Preferably, the reaction should be conducted within the temperature limits of about 27° C. to about 74° C.

Experimental Apparatus and Procedure

The reaction vessel used in the following Examples was a one-liter, round bottom, four-necked flask. The center neck was fitted with a hollow shaft rotatable stirring rod. A stirrer blade provided agitation. A dip leg, of capillary-bore tubing, fitted with a glass joint and stopcock was inserted into another neck to serve for withdrawing samples. A straight tube, water cooled condenser, and a standard taper thermometer completed the assembly. The apparatus was painted black to exclude light. Chlorine gas was metered into the reactor via the hollow glass stirring rod.

The reactor was immersed in a water bath to provide for holding the reaction mass at constant temperature.

Catalyst Preparation $MnCl_2$ was charged to a 100 milliliters flask fitted wth a reflux condenser. Sufficient thionyl chloride was added to cover the salt. The mixture was heated until evolution of HCl and $SO_2$ ceased. Excess $SOCL_2$ was decanted from the $MnCl_2$ and that retained in the mass of salt was removed under heat and vacuum.

Five hundred grams of benzene and/or monochlorobenzene was charged to the reaction flask. Chlorine gas was fed at a rate to satisfy demand. Samples of the reactor contents were periodically withdrawn during the course of the reaction and analyzed by gas-liquid chromatography. Unless specified otherwise, the reaction temperature used was 50° C., the catalyst concentration was 0.1 percent and all proportions of materials were on a weight basis.

EXPRESSION OF EXPERIMENTAL RESULTS

Experimental results are discussed in two aspects:
1. The proportion of dichlorobenzene isomers, the p/o ratio;
2. The chlorination rate, $\Delta x/\Delta t$; where $x$ is defined as the degree of substitution or the gram atoms of chlorine per mole of combined product including unreacted benzene; $t$ equals time in hours.

In order to make a comparison of the data, the p/o ratio is calculated at an arbitrary $x$ value of 1.50.

EXAMPLE I

Employing the laboratory apparatus and experimental procedures described in the preceding sections, a series of experiments were performed. The results are shown in Table 1.

TABLE 1

CHLORINATION CATALYSTS

| Experiment No. | 1 | 2 | 3 | 4 | 5 | 6 | 7 | 8 |
|---|---|---|---|---|---|---|---|---|
| Catalyst[1] | Mn-1 | Mn-1 | Mn-2 | Fe and Mn-1 | Fe | U | Mn-1 | Fe |
| Feed[2] | B | B | B | B | B | B | MCB | MCB |
| $\Delta x/\Delta t$ | .174 | .180 | .042 | .300 | .287 | .003 | .160 | .313 |
| p/o Ratio[3] | 1.13 | 1.06 | 1.22 | 1.44 | 1.76 | Erratic | 1.02 | 1.40 |
| Moisture (ppm) | — | — | — | — | — | — | 97 | 98 |

[1]Catalyst Sources Mn-1 is reagent grade $MnCl_2 \cdot 4H_2O$ dehydrated with $SOCl_2$. Mn-2 is $MnCl_2$ flaked from a melt (contains little water) and dehydrated with $SOCl_2$. Fe and Mn-1 is catalyst Mn-1 admixed with $FeCl_3$ (0.1 mole percent Mn-1 and 500 ppm $FeCl_3$). Fe is reagent grade $FeCl_3$. U is an uncatalyzed reaction.
[2]Feed B = benzene MCB = monochlorobenzene
[3]p/o at x = 1.5.

The experimental results show that manganese chloride catalyst composition give low p/o ratios, in particular, catalyst compositions prepared by dehydrating hydrous $MnCl_2$ give good rates of reaction together with low p/o ratios for both benzene and monochlorobenzene feedstocks. In contrast, iron-containing catalysts yield acceptable reaction rates with relatively high p/o ratios. Data for an uncatalyzed reaction is provided for a comparison.

EXAMPLE II

This example illustrates the effects of both moisture and the presence of iron on the p/o ratio of the dichlorobenzene reaction product. The experimental procedure and apparatus of Example I were used. The catalyst is Mn-1 of Example I. The experimental results are shown in Table 2.

TABLE 2

| Experiment No. | Moisture ppm | Fe ppm as $FeCl_3$ | p/o Ratio at x = 1.50 |
|---|---|---|---|
| 9 | 45 | 1 | 1.189 |
| 10 | 45 | 7 | 1.390 |
| 11 | 147 | 1 | 1.063 |
| 12 | 147 | 7 | 1.509 |

The presence of moisture encourages low p/o ratios. The presence of iron yields high p/o ratios (about 1.4). Moisture and iron interact to give high p/o ratios.

EXAMPLE III

This example illustrates the influence of temperature on the para-/ortho-isomer ratio in a manganese chloride catalyzed liquid phase process. The experimental procedure and apparatus is that used in Example I. The catalyst is Mn-1 of Example I. The results are set out in Table 3.

TABLE 3

EFFECT OF TEMPERATURE

| Experiment | 13 | 14 | 15 | 16 | 17 |
|---|---|---|---|---|---|
| Temperature, °C. | 25° | 40° | 50° | 60° | 70° |
| Mean p/o Ratio | 1.50 | 1.25 | 1.06 | 1.24 | 1.32 |
| Mean $\Delta x/\Delta t$ | 0.140 | 0.166 | 0.180 | 0.153 | 0.197 |

A curve drawn through the data of Table 3 indicates that p/o ratios less than 1.35 are attained by operating the process of this invention at temperatures between about 27° C. and about 74° C. Interpolation of the data points shows an optimum reactor temperature in the vicinity of 50° C.

EXAMPLE 4

Part A

Manganese chloride catalyst compositions produce less polychlorinated benzene products for a given quantity of desired ortho- and para- dichlorobenzenes than conventional $FeCl_3$ catalysts. Experimental results are shown in Table 4. The apparatus and procedure of Example II were used.

Part B

Manganese chloride catalyst compositions reduce dichlorobenzene isomer separation problems by yielding a lower ratio of meta to para isomer. The apparatus and procedure of Example II were used. Experimental results are shown in Table 4.

TABLE 4

| | Monochlorobenzene Feedstock, 99.99+% Purity Adjusted to 97 ppm H₂O, MnCl₂ Catalyst | | | | | Monochlorobenzene Feedstock, 99.99+% Purity Adjusted to 89 ppm H₂O, FeCl₃ Catalyst | | |
|---|---|---|---|---|---|---|---|---|
| Sample No. | 18 | 19 | 20 | 21 | 22 | 23 | 24 | 25 |
| Running Time, Hours | 1.00 | 2.00 | 3.00 | 4.00 | 5.00 | 1.42 | 3.33 | 5.835 |
| Composition, Weight percent | | | | | | | | |
| Monochlorobenzene | 86.8 | 67.4 | 47.7 | 30.2 | 16.2 | 52.8 | 3.03 | — |
| Meta Dichlorobenzene | 0.23 | 0.55 | 0.77 | 0.99 | 1.16 | 1.45 | 1.68 | — |
| Para Dichlorobenzene | 6.73 | 16.1 | 25.6 | 34.1 | 40.9 | 26.2 | 50.1 | 25.9 |
| Ortho Dichlorobenzene | 6.14 | 15.7 | 25.4 | 33.6 | 39.7 | 18.8 | 35.1 | 2.57 |
| Combined $C_6H_3Cl_3$ | 0.0527 | 0.219 | 0.47 | 1.06 | 2.15 | 0.80 | 9.89 | 54.79 |
| Combined $C_6H_2Cl_4$ | 0.017 | 0.025 | 0.0206 | 0.048 | 0.084 | — | 0.149 | 16.59 |
| CHLORINATION LEVEL "X" | 1.105 | 1.272 | 1.459 | 1.647 | 1.818 | 1.411 | 2.043 | 2.796 |
| Ratio of Metadichlorobenzene to Paradichlorobenzene | 0.034 | 0.034 | 0.030 | 0.029 | 0.028 | 0.055 | 0.034 | — |
| Ratio of Combined $C_6H_3Cl_3$ and $C_6H_2Cl_4$ to Para and Ortho Dichlorobenzenes | 0.0054 | 0.0076 | 0.0096 | 0.0164 | 0.0277 | <0.0177 | 0.1178 | 2.5019 |
| Combined Para and Ortho Dichlorobenzenes, Weight Percent | 12.87 | 31.8 | 51.0 | 67.7 | 80.6 | 45.0 | 85.2 | 28.47 |

EXAMPLE 5

This example shows the effect of catalyst concentration on reaction rate ($\Delta x/\Delta t$). The apparatus and experimental procedure of Example II were used. Table 5 displays the results:

The chlorination rate ($\Delta x/\Delta t$) is interpolated to be less than a practical level at catalyst concentrations under at least 0.05 weight percent.

TABLE 5

EFFECT OF CATALYST CONCENTRATION (OR AMOUNT OF SURFACE)[1]

| Sample No. | Manganese Chloride[2] Catalyst Level | $\Delta x / \Delta t$ (Initial) | p/o Ratio |
|---|---|---|---|
| 26 | 0.0 (Uncatalyzed) | 0.0029 | (Very low, but erratic |
| 27 | ~ 4 ppm as Mn[3] | 0.0139 | 1.075 |
| 28 | 0.164% by weight | 0.180 | 1.06 |
| 29 | 0.334% | 0.324 | 1.08 |
| 30 | 0.487% | 0.400 | 1.08 |

[1]All values are for chlorination of benzene at 50° C.
[2]MnCl₂ (anhydrous), Mn-1 of Example I.
[3]In this experiment, there was no solid phase of MnCl₂. 4 ppm is the level of manganese retained by a crude chlorinated benzene product using the process of this invention. The product was filtered hot and later recharged into the cleaned reaction vessel.

Although the present invention has been described with reference to the specific details of particular embodiments thereof, it is not intended to limit the scope of the invention except insofar as the specific details are recited in the appended claims.

We claim:

1. A process for preparing a dichlorobenzene product having a mole ratio of paradichlorobenzene to orthodichlorobenzene below 1.35, which comprises reacting benzene or monochlorobenzene and elemental chlorine in the liquid phase, in the presence of a catalytically effective amount of a manganese chloride catalyst composition, at a temperature between about 27° C. to about 74° C., the reaction media having an iron concentration not above about 3 parts per million.

2. A process for preparing a dichlorobenzene product having a mole ratio of paradichlorobenzene to orthodichlorobenzene below 1.35, which comprises reacting benzene or monochlorobenzene and elemental chlorine in the liquid phase, in the presence of a catalytically effective amount of a catalyst composition consisting essentially of manganese chloride, at a temperature between about 27° C. to about 74° C., the reaction media having an iron concentration not above about 3 parts per million.

3. The process of claim 1 wherein a catalyst composition concentration sufficient to provide at least 0.05 percent by weight of anhydrous manganese chloride based on the weight of liquid media in the reaction zone is used.

4. The process of claim 1 wherein the benzene or monochlorobenzene feed introduced to the reaction zone contains about 10 to about 500 parts per million of water.

5. The process of claim 1 wherein the reaction is conducted in the absence of catalytically effective amounts of chlorination catalysts which promote a paradichlorobenzene to orthodichlorobenzene mole ratio of about 1.4 or above.

6. A process according to claim 1 wherein the manganese chloride catalyst composition is introduced to the reaction zone in substantially anhydrous form.

7. A process according to claim 1 wherein the manganese chloride catalyst composition is hydrated.

8. A process according to claim 7 wherein the manganese chloride contains between 0.8 and 1.5 moles of water of hydration.

9. The process of claim 1 for the nuclear chlorination of monochlorobenzene to form a dichlorobenzene product.

10. The process of claim 1 for the nuclear chlorination of benzene to form a dichlorobenzene product.

11. The process of claim 1 wherein catalytically effective amounts of compounds derived from aluminum, sulfur, gallium, molybdenum, tin, antimony, tellurium, samarium, zinc, copper, phosphorus and iodine are excluded from the reaction medium.

12. The process of claim 1 wherein catalytically effective amounts of compounds derived from copper are excluded from the reaction medium.

13. The process of claim 2 for the liquid phase chlorination of monochlorobenzene to form a dichlorobenzene product.

14. The process of claim 2 for the liquid phase chlorination of benzene to form a dichlorobenzene product.

* * * * *